United States Patent [19]

Bentkowski

[11] Patent Number: 4,476,722
[45] Date of Patent: Oct. 16, 1984

[54] CONTINUOUSLY MONITORING AND SELF-CLEANING LIQUID DENSITY MEASUREMENT SYSTEM

[75] Inventor: James E. Bentkowski, Oklahoma City, Okla.

[73] Assignee: Scientific Resources, Inc., Oklahoma City, Okla.

[21] Appl. No.: 426,955

[22] Filed: Sep. 29, 1982

[51] Int. Cl.³ .............................................. G01N 9/06
[52] U.S. Cl. ..................................................... 73/434
[58] Field of Search .................................. 73/433, 434

[56] References Cited
U.S. PATENT DOCUMENTS

| | | | |
|---|---|---|---|
| 2,284,060 | 5/1942 | Knauth | 73/434 |
| 2,311,312 | 2/1943 | Marsh | 73/434 |
| 2,613,530 | 10/1952 | Nichols | 73/434 |
| 2,669,118 | 2/1954 | Nichols | 73/434 |

Primary Examiner—S. Clement Swisher
Attorney, Agent, or Firm—Stevens, Davis, Miller & Mosher

[57] ABSTRACT

An apparatus for measuring density of drilling mud. An elongated cylindrical measuring chamber is pivoted on a base at one end and includes conduits for introducing the mud into the chamber. A force measuring thrust a gauge mounted on the base and supporting the chamber intermediate its ends provides a signal proportional to the weight of the receptacle and its contents. Since the volume of the chamber is constant the weight varies as a function of the density of mud. A rotating wire brush mounted within the chamber tends to scrape away accumulating solid material on the inner walls thereof. The chamber is provided with a ceramic liner.

10 Claims, 3 Drawing Figures

CONTINUOUSLY MONITORING AND SELF-CLEANING LIQUID DENSITY MEASUREMENT SYSTEM

This invention relates to an apparatus for continously measuring the density or weight of a liquid in or passing through a measurement system.

BACKGROUND OF THE INVENTION

The necessity to measure the density of a liquid is widespread throughout the processing, mining and petro-chemical industries. Many systems have been developed to try to obtain an accurate and continuous measurement of a constantly changing weight of a liquid. If the liquid is stationary in the measuring instrument or of a particular consistency then deposits can form on the inner walls causing a build-up of material and an eventual erroneous measurement. Some instruments measure a constant flow of liquid therethrough, however many liquids, particularly those used in oil well drilling, will still form a coating or build-up within the instrument.

Many instruments employ a U-tube type sensing device, or tube container. As pointed out in U.S. Pat. No. 3,370,471, U-tube type densitometers are known for their instability and problems. Also, U-tube type densitometers are sensitive to the flow rate. Higher flow rates can result in liquid turbulence and centrifuging of the liquid while lower flow rates can result in the suspended heavier particles settling out of the liquid and building up on the inside of the densitometers.

Another problem encountered with U-tube type devices and other known devices is the use of flexible couplings of flexible tubing to connect the measurement device to the instrument. In U.S. Pat. No. 4,285,239, it is stated: "Nuclear densitometers and weight measuring type densitometers suffer certain inherent shortcomings. Nuclear densitometers work rather poorly when the density of the slurry is not uniform throughout the crossection of the pipe. The prior art weight measuring type densitometers on the other hand, are, generally speaking, unable to accurately determine the true weight of a given pipe section because of the inherent structural problem that the pipe section must be physically coupled to the pipeline. Various types of flexible joints were used for this purpose in prior art," and such are discussed in U.S. Pat. Nos. 3,503,267; 3,320,791; 688,388; 2,039,997; 2,613,530; 2,669,118; 3,812,723; 3,143,887; 1,905,558; 3,004,544; 3,039,310; 3,044,302; 3,151,775; 3,187,584; 3,020,765; 3,225,603; 3,258,973; 3,320,791; 3,330,161; 3,431,785 and 3,473,368. The above mentioned prior art have inherent problems due to the use of flexible couplers. Much effort and expense have been devoted toward the development of an accurate and dependable liquid weight measuring device.

Another inherent problem is that of material build-up inside the instrument or weight-measuring device. To overcome a material build-up attempts have been made to build a self-cleaning instrument. U.S. Pat. No. 3,320,791 discloses a device that is self-cleaning. However, a U-tube type device is employed in one application and flexible couplers, or bellows, in another application. Due to the required insertion of a semirigid tube or rod into the system, if the build-up is too great it results in deformation of the rod and tube or precludes insertion of the rod at all. Also, if the tube is processing sandfilled or corrosive liquids the sides of the tubes will be worn and the cleaning rod will not clean the inner walls when inserted.

U.S. Pat. No. 2,311,312 and U.S. Pat. No. 2,708,360 clean the tube by means of a flushing action. However, both of these devices use a flexible coupling as previously discussed. Also, in many instances it is not possible to flush the liquid being measured with another liquid due to contamination of the liquid being measured. The chemical industry is most familiar with this problem such as flushing an acid-based liquid with water. Therefore, flushing type systems are not always desirable or practical. In U.S. Pat. Nos. 3,320,790, 2,311,312 and 2,708,360, it is necessary to interrupt the normal flow of the liquid in order to clean or flush the weight measured liquid. Also, high flow velocities cannot be used with some slurries or liquids as the flow will become turbulent resulting in erroneous measurements. To date, prior art densitometers have not been able to overcome the combined problems common to U-tubes, flexible couplings and maintaining self-cleanliness.

It is therefore an object of this invention to provide a liquid weight measurement instrument which will accurately measure the density of the liquid in, or flowing through, the instrument.

Another object of this invention is to provide such a weight measurement instrument that is self-cleaning and therefore not subject to erroneous measurements due to sedimentation or build-up in the instrument.

A further object of this invention is to provide a liquid weight measurement instrument that is self-cleaning during the normal operation of the system so that no interruption of the measurement results during the cleaning cycle.

A still further object is to provide an instrument that is sensitive, accurate and versatile yet rugged and inexpensive and easy to manufacture. Another object of this invention is to provide an instrument which will eliminate problems encountered with earlier densitometers of U-tube type design and densitometers using flexible couplings within the measurement device.

SUMMARY OF THE INVENTION

The measuring system of the present invention is comprised of a container pivoted at one end to a base, weight measuring mechanism attached to the container intermediate the pivot and its other end and a means to clean the interior of the container without effecting the measurements while the liquid to be measured is within the container in a static state or flowing therethrough.

BRIEF DESCRIPTION OF THE DRAWINGS

Other details and features of the invention will stand out from the description given below by way of nonlimitative example and with reference to the accompanying drawings, in which.

DESCRIPTION OF THE PREFERRED EMBODIMENT

Figure 1:
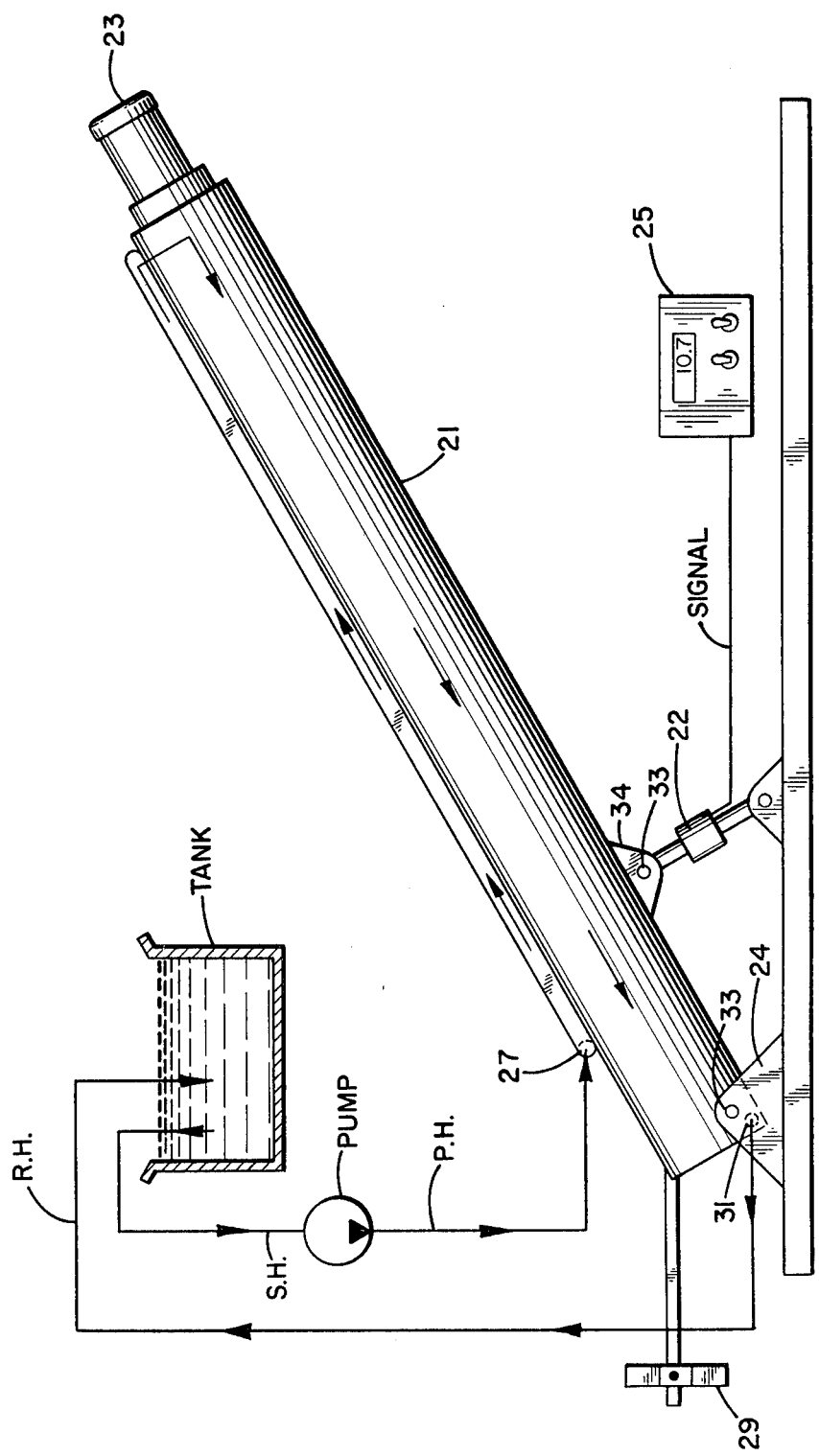
FIG. 1 is a perspective presentation of the principle components of the present invention.

FIG. 1 shows a container 21 attached to a base 24 in such a manner that it can move pivotally around bearing 30. A conventional liquid pump PM moves the liquid from the tank TK via suction hose SH into the container 21 at input port 27 returning to tank TK via exit port 31 and return hose RH. Although the pressure hose PH and the return hose RH may be of a flexible type, since they attach at a point that is vertically in line with bearing 30 they will have no effect upon the weight measuring mechanism or its linear response. Or, if desired, these lines may be attached with fixed tubing and/or rotary ball couplings. A weight measuring mechanism 22 is connected to container 21 at bracket 34 such that it can move pivotally around bearing 33. The weight bearing mechanism sends a signal to a monitoring and display unit 25 which constantly registers the information sought. It will be understood by those skilled in the art that the pump PM can be of several types and be driven by several means, such as electrical, hydraulic or pneumatic motors. It will also be understood that the rate of the liquid passing through the container 21 can be controlled by several means already in common use in the industry: flow valves, variable speed motors or liquid level sensors in container 21. It is understood by those of skill in the art that the weight measuring mechanism 22 may be of a variety of types, such as hydraulic compression or tension load cells, mechanical sensors, strain gage, electronic or other weight measuring mechanisms well known and used in the art. The linearity of the forces applied against the weight measuring mechanism will also be understood by those knowledgeable in the art. If so desired, a counterbalance 29 may be attached to container 21 to offset or nullify the weight of the container 21 and associated equipment to result in no weight being registered on the weight measuring mechanism 22 for the equipment. As alternatives, an electronic nullifier or other well known means may be used.

Figure 2:
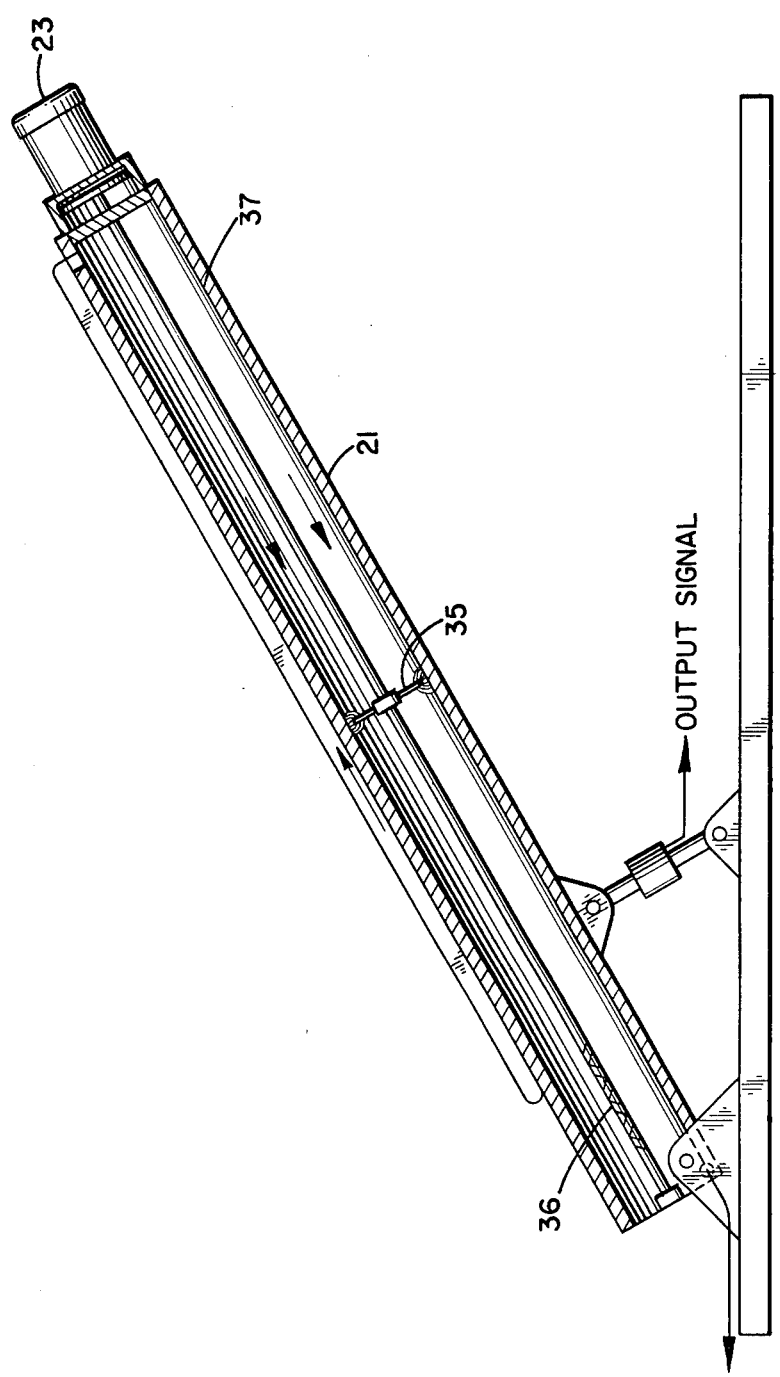
FIG. 2 is a cutaway presentation of the principle components of the present invention.

In FIG. 2 motor 23 is used to power a cleaning brush 35 inside container 21 to avoid build-up of materials on the inner walls of container 21. The brush 35 is of a disk type mounted to reciprocate on a shaft 36 which extends from the motor 23 to the other end of the container 21. The brush also may be cylindrical in design and extend from the motor to the other end of the container 21. It will be understood by those of skill in the art that motor 23 can be of a variety of types and controlled by external means and circuits. When motor 23 is actuated the cleaning brush 34 cycles through container 21 scrubbing the cake and particles from the sides of container 21 as well as scrubbing the brush 35 itself. The loose particles are then passed out through container 21 out through outlet 31 into tank TK via return hose RH. This cleaning action can occur while the weight measurement system is in normal operation without effecting the accuracy of the system. It will be understood that the surface area of the cleaning brush 35 and associated cleaning apparatus is small in area as compared with the surface area of the inner walls of the container 21. Any build-up of materials on the cleaning apparatus will be dislodged during the cleaning cycle and the weight of the remaining residue will be negligible as compared with the volume sampled. Also, if desired, a ceramic liner 37 or other type of liner may be used in container 21. A ceramic liner prevents the temperature of the liquid from adversely affecting the accuracy of the system. This may aid in creating a smoother, stronger and longer lasting device and the liner can be replaced if damaged or worn. However, any addition of equipment does not change the scope or weight measuring capabilities of the present invention. Due to the design of the present invention and the implementation of the age-old application of mechanical advantage it will be understood that a unit of this design can be built to measure the weight of a liquid ranging from a minute amount to a very large amount.

Figure 3:
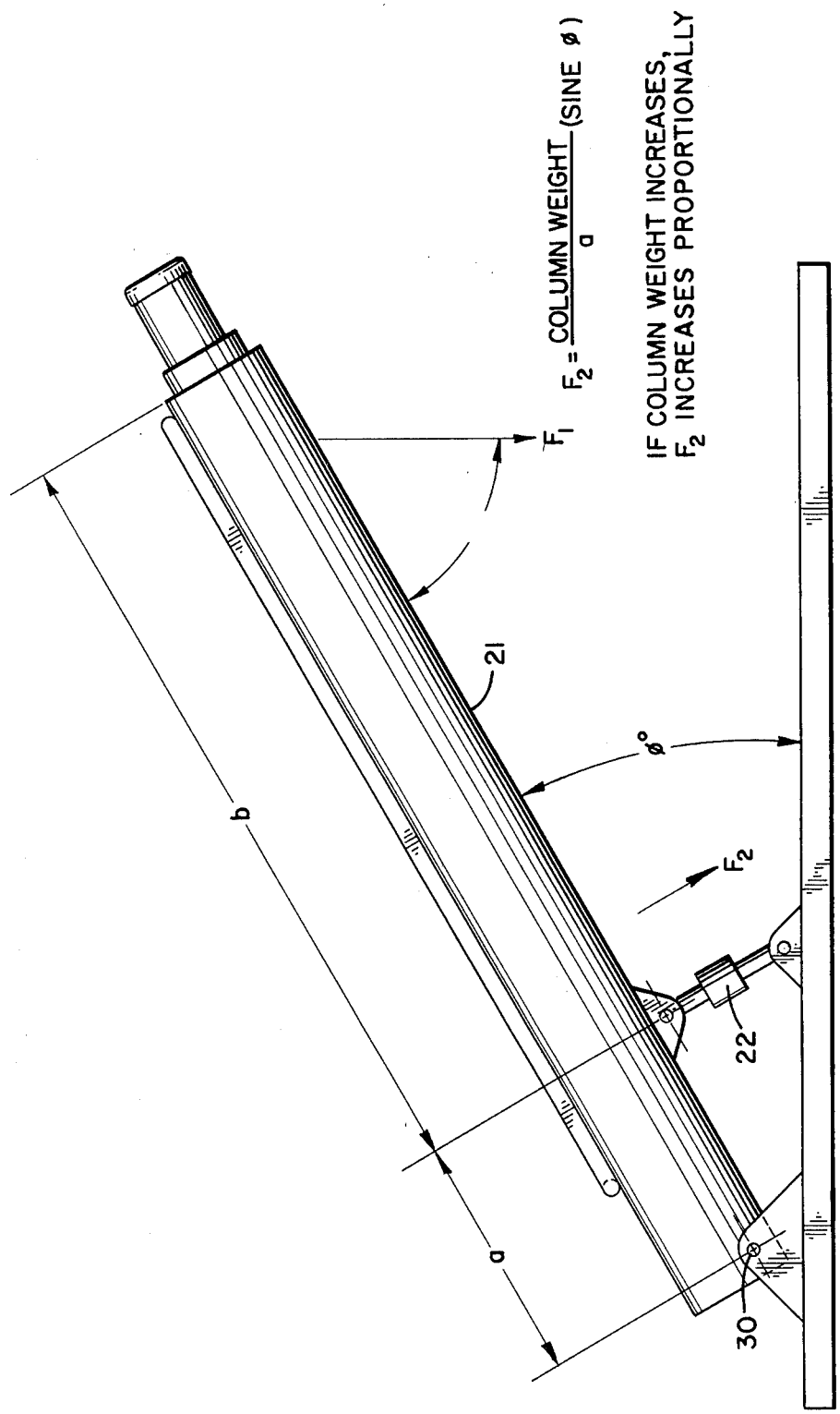
FIG. 3 is an engineering drawing showing the infinite number of possibilities relating to the mechanical advantages of the present invention and the laws of mechanical engineering which have been applied.

In FIG. 3, from an engineering perspective, it will be obvious to those knowledgeable in the art that the weight of a liquid inside, or passing through, container 21 will have a liner and proportional effect upon the force applied on the weight measuring mechanism. Through this design, flexible hoses can be attached to container 21 at the pivot point bearing 30 with no change to the liner response of the weight measuring mechanism 22. The angle between the weight measuring mechanism 22 and container 21 can be changed to an infinite degree thus allowing the measurement of a variety of liquids of different weights and therefore implementing the use of a variety of types and sizes of weight measuring mechanisms.

What is claimed is:

1. A system for continuously monitoring and measuring the actual physical weight or density of a liquid whether the liquid is in a static state or flowing state comprising a base, a container having two ends pivotable thereto and through which the liquid flows, a weight measuring mechanism attached to said container to measure the weight of the liquid in said container and means within said container to avoid build-up of material inside said container.

2. The system according to claim 1 including a monitoring and display unit and wherein said weight measuring mechanism sends resultant linear output signals to said unit.

3. The system according to claim 1 wherein the container holds a fixed volume of liquid, at any given time, and when the weight of said liquid changes, the force applied against said weight measuring mechanism changes linearly and proportionally.

4. The system according to claim 1 wherein said means to remove material build-up on the inner walls of said container can do so without adversely effecting the operation of said system.

5. The system according to claim 1 wherein said container and said weight measuring mechanism are pivotally mounted relative to each other so that liquids of different densities may be measured.

6. The system according to claim 1 wherein said means to avoid build-up of material in said container is a brush operable without interrupting the flow of the liquid in said container and without interrupting the weight measurement of the liquid in said container.

7. The system according to claim 1 including inlet and outlet ports on said container positioned vertically above and below said container pivot.

8. The system according to claim 1 including a counterweight and wherein said container is pivoted at one end thereof, said counterweight being attached to an end of said container nearest to said pivot to counterbalance the weight of said container.

9. The system according to claim 1 including a removable liner within said container, said liner having a smooth surface to assist in avoiding the build-up of material on the surface of said container.

10. The system according to claim 9 wherein said liner is of a ceramic material such that the temperature of said liquid will not adversely affect the accuracy of said system.

* * * * *